United States Patent [19]

Sidot et al.

[11] Patent Number: 4,810,822

[45] Date of Patent: Mar. 7, 1989

[54] PURE ANHYDROUS CRYSTALLIZED ACRYLAMIDOGLYCOLIC ACID AND A METHOD FOR THE PREPARATION THEREOF

[75] Inventors: Christian Sidot, Ezanville; Yani Christidis, Paris, both of France

[73] Assignee: Societe Francaise Hoeschst, Puteax, France

[21] Appl. No.: 208,787

[22] Filed: Jun. 15, 1988

Related U.S. Application Data

[63] Continuation of Ser. No. 33,822, Apr. 3, 1987.

[30] Foreign Application Priority Data

Mar. 16, 1987 [FR] France .................................. 87 03545

[51] Int. Cl.$^4$ ................. C07C 103/133; C07C 102/04
[52] U.S. Cl. .................................................. 562/567
[58] Field of Search ........................................ 562/567

[56] References Cited

U.S. PATENT DOCUMENTS

| | | | |
|---|---|---|---|
| 3,422,139 | 1/1969 | Talet et al. | 562/567 |
| 3,444,124 | 5/1969 | Talet | 562/567 |
| 4,105,690 | 8/1978 | Christidis et al. | 562/567 |
| 4,443,623 | 4/1984 | Photis | 560/170 |

*Primary Examiner*—Bruce D. Gray
*Attorney, Agent, or Firm*—Browdy & Neimark

[57] ABSTRACT

This acid is prepared by a method comprising reacting acrylamide with glyoxylic acid in an aqueous solution at a concentration equal to or higher than 60% and at a temperature of between 30° C. and 80° C., this method being characterized in that this reaction is carried out at a pH of less than 7, in the absence of a catalyst of any type whatsoever but in the presence of an organic solvent selected from the group comprising ethyl acetate, butyl acetate, acetone, methyl ethyl ketone, methyl isobutyl ketone, tetrahydrofuran, diethylene glycol dimethyl ether.

5 Claims, No Drawings

PURE ANHYDROUS CRYSTALLIZED ACRYLAMIDOGLYCOLIC ACID AND A METHOD FOR THE PREPARATION THEREOF

This application is a continuation of application Ser. No. 033,822, filed Apr. 3, 1987.

BACKGROUND OF THE INVENTION

The present invention relates to pure anhydrous crystallized acrylamidoglycolic acid and a method for the preparation thereof.

PRIOR ART

French Patent No. 1.411.715 describes crystallized acrylamidoglycolic acid with one molecule of water. This acid, which has a melting point of 95° C., is insoluble in chlorinated solvents and non-polar solvents; moreover, it is not very soluble in acrylic monomers.

The method generally used for its preparation involves causing glyoxylic acid to react with acrylamide in an aqueous solution at an alkaline pH in the presence of a catalyst, for example sodium carbonate.

Anhydrous crystallized acrylamidoglycolic acid has for a long time been the subject of research but all attempts at desolvation of crystallized acrylamidoglycolic acid with one molecule of water have foundered on the instability of this acid.

Accordingly, the expectations in respect of anhydrous crystallized acrylamidoglycolic acid have not yet been fulfilled, particularly with a view of the possibility of readily incorporating it in vinyl or acrylic copolymers in non-aqueous solution or dispersion. In fact, this acid is a cross-linking monomer which imparts acid funtions of an original nature to the copolymers containing it.

SUMMARY OF THE INVENTION

The Applicants have now discovered that it is possible to prepare, in an advantage manner, pure anhydrous crystallized acrylamidoglycolic acid with a high yield by reacting under certain conditions glyoxylic acid with acrylamide. Pure anhydrous crystallized acrylamidoglycolic acid is obtained directly, without the necessity of applying subsequent treatments to effect its purification. It exhibits excellent stability during storage, it is not hygroscopic and it is absolutely colourless.

The invention relates to pure anhydrous crystallized acrylamidoglycolic acid.

The invention also concerns a method of preparing pure anhydrous crystallized acrylamidoglycolic acid by reacting acrylamide with glyoxylic acid in an aqueous solution at a concentration equal to or higher than 60% and at a temperature of between 35° C. and 80° C., this method being characterized in that the reaction is carried out at a pH of less than 7 in the absence of a catalyst of any type whatsoever.

DETAILED DESCRIPTION OF THE INVENTION

It is surprising that the condensation between acrylamide and glyoxylic acid can take place at a pH of less than 7, since it is generally accepted that this type of N-methylolation reaction of amide groups requires an alkaline pH.

Preferably, the method described above is carried out in a compatible organic solvent partly soluble in water, such as ethyl acetate, butyl acetate, acetone, methyl ethyl ketone, methyl isobutyl ketone, tetrahydrofuran, diethylene glycol dimethyl ether.

The following example illustrates the invention but does not imply any limitation thereof.

EXAMPLE 213 g (3 moles) of acrylamide are introduced slowly, over a period of about 5 minutes, to a stirred solution composed of:
277 g of ethyl acetate,
277 g of an aqueous solution of glyoxylic acid at 80% by weight, namely 3 moles of glyoxylic acid,
0.24 g of hydroquinone monomethyl ether.

The dissolution of the acrylamide takes place endothermically. The resultant solution is then heated at about 50° C. for 210 minutes, then it is cooled to room temperature. The anhydrous acrylamidoglycolic acid crystallizes spontaneously. It is drained, then washed by trituration with chilled ethyl acetate and, finally, it is dried under vacuum at 35° C. to constant weight.

340 g (2.34 moles) of colourless, pure anhydrous crystallized acrylamidoglycolic acid are thus obtained, having an instantaneous melting point of 125±2° C. with decomposition, namely a theoretical yield of 78%.

| | Microanalysis | | | |
| --- | --- | --- | --- | --- |
| | C % | H % | N % | O % |
| $C_5H_7NO_4$ calculated | 41.37 | 4.86 | 9.65 | 44.12 |
| MW = 145.11 found | 41.6 | 4.9 | 9.7 | | acidimetric determination:100%
determination of double bonds:100%

The solubility of this acid is 12% in water, 0.25% in ethyl acetate, 2.5% in acetone and 0.25% in butyl acrylate.

As far as the Applicants are aware, this product has not been described in the prior art.

It is to be understood that the present invention has only been described by way of example and without limitation, and that any modification, particularly insofar as equivalents are concerned, could be made thereto without departing from the scope thereof.

We claim:

1. Pure anhydrous crystallized acrylamidoglycolic acid.

2. Method of preparing pure anhydrous crystallized acrylamidoglycolic acid by reacting acrylamide with glyoxylic acid in an aqueous solution at a concentration equal to or higher than 60% and at a temperature of between 30° C. and 80° C., wherein said reaction is carried out at a pH of less than 7 in the absence of a catalyst of any type whatsoever.

3. Method according to claim 2, carried out in the presence of an organic solvent selected from the group consisting of ethyl acetate, butyl acetate, acetone, methyl ethyl ketone, methyl isobutyl ketone, tetrahydrofuran, diethylene glycol dimethyl ether.

4. A method of preparing pure anhydrous crystallized acrylamidoglycolic acid, comprising:
reacting glycolic acid in an aqueous solution at a concentration of at least 60% with acrylamide in a reaction medium at a temperature between 30° C. and 80° C. and a pH of less than 7 in the absence of a catalyst of any type whatsoever.

5. A method according to claim 4 wherein said reaction medium comprises an organic solvent selected from the group consisting of ethyl acetate, butyl acetate, acetone, methyl ethyl ketone, methyl isobutyl ketone, tetrahydrofuran, and diethylene glycol dimethyl ether.

* * * * *

UNITED STATES PATENT AND TRADEMARK OFFICE
CERTIFICATE OF CORRECTION

PATENT NO. : 4,810,822
DATED : March 7, 1989
INVENTOR(S) : SIDOT et al.

It is certified that error appears in the above-identified patent and that said Letters Patent is hereby corrected as shown below:

On the face of the Patent:

[73] Assignee:  Delete "Hoeschst, Puteax", insert therefor -- Hoechst, Puteaux --

Signed and Sealed this

Twenty-fourth Day of December, 1991

Attest:

HARRY F. MANBECK, JR.

*Attesting Officer*  *Commissioner of Patents and Trademarks*